US005526962A

United States Patent [19]
Huggenberger

[11] Patent Number: 5,526,962
[45] Date of Patent: Jun. 18, 1996

[54] DOUBLE PISTON PUMP FOR ADMINISTERING MEDICATION

[75] Inventor: Heinz Huggenberger, Grafenried, Switzerland

[73] Assignee: Medimpex Ets., Balzers, Liechtenstein

[21] Appl. No.: 241,139

[22] Filed: May 10, 1994

[30] Foreign Application Priority Data

May 10, 1993 [CH] Switzerland .................. 01432/93

[51] Int. Cl.⁶ ............................................. G01F 11/00
[52] U.S. Cl. ............................. 222/276; 417/535
[58] Field of Search ....................... 222/249, 250, 222/275, 276, 265, 409, 383, 383.1; 417/415, 534, 535

[56] References Cited

U.S. PATENT DOCUMENTS

| 218,245 | 8/1879 | Duwelius | 417/535 |
|---|---|---|---|
| 664,947 | 1/1901 | Hanna | 417/535 X |
| 1,854,773 | 4/1932 | Tannehill | 417/535 X |
| 2,023,250 | 12/1935 | Stalder | 417/535 X |
| 2,998,164 | 8/1961 | Clements | 222/275 X |
| 3,216,627 | 11/1965 | Best et al. | 222/249 |
| 4,149,658 | 4/1979 | Teufel | 222/276 X |
| 4,394,940 | 7/1983 | Peterson | 222/276 |
| 4,443,163 | 4/1984 | Gaither | 417/534 X |
| 4,512,188 | 4/1985 | Erickson | 222/276 X |
| 5,058,768 | 10/1991 | Lichfield | 222/276 X |
| 5,076,769 | 12/1991 | Shao | 417/534 |
| 5,390,585 | 2/1995 | Ryuh | 417/534 X |

FOREIGN PATENT DOCUMENTS 136680  12/1919  United Kingdom .................. 417/534

*Primary Examiner*—Kevin P. Shaver
*Attorney, Agent, or Firm*—Walter C. Farley

[57] ABSTRACT

The device of the invention provides preselected doses of liquid medicine and has a cylinder assembly (1, 2) with a left cylinder (1), a right cylinder (2) and a double piston (4, 5) displaceably mounted in the assembly with a left piston end (4) and a right piston end (5). A coupling links the double piston in a positive and/or frictional manner with a drive unit (15). The device is controlled passively by two automatically closing intake valves (7, 8) and two discharge valves (11, 12). Thereby a continuous flow of liquid medicine 20 out of the medicine container 10 can be generated.

13 Claims, 2 Drawing Sheets

DOUBLE PISTON PUMP FOR ADMINISTERING MEDICATION

FIELD OF THE INVENTION

This invention concerns a device for administering a dose of preselected quantity of liquid medicine to a patient, or a sequence of such doses.

BACKGROUND OF THE INVENTION

The German Offenlegungsschrift 40 16 306 discloses a radial piston pump to supply small amounts of liquid, wherein two independent pump pistons are driven in mutually opposite directions and implement conveyance of the liquid through controlled valves. This known radial pump has the drawbacks of inherent high transverse forces and entailed friction and also requires high manufacturing accuracy of the cooperating radial disks.

SUMMARY OF THE INVENTION

An object of the invention is to provide an improved dosing apparatus and specifically an easily handled device to supply a preselected dose of liquid medicine and permitting accurate dispensing and variation of the medicine dose.

This object is achieved in accordance with the invention by a device a cylinder with a left cylinder part and a right cylinder part, with a double piston displaceably mounted therein and comprising left and right piston parts and means for linkup-up in positive and/or frictional manner with a drive unit, the device being passively controlled by two sets of two automatically closing intake and outlet valves.

Essentially the advantages achieved by the invention are as follows:

- because of the double piston, the system never experiences a partial vacuum; a steady flow of medicine takes place in operation;
- because the pump unit and the drive unit are separate and easily and quickly can be joined together, handling is simple and patient-friendly;
- the dispensing quality is determined by the pump itself on account of the injection-molded plastic parts of the pump unit, rather than by external parameters such as pressure, temperature, humidity and the like;
- changes in medicine doses can be preset by pump-unit parameters (piston diameter) and the pitch of the thread of the piston rod: as a result, a corresponding standard set of pump units can be set up;
- the drive unit can be used for a substantial time, i.e., it may be used for several medicine containers of one patient;
- the pump unit is designed as a one-way system for single use; and
- the device is secured against the patient removing liquid medicine from the medicine container.

BRIEF DESCRIPTION OF THE DRAWINGS

The drawings show an illustrative embodiment of the invention together with the principle of operation which will be described with reference to the following drawings wherein.

DESCRIPTION OF THE PREFERRED EMBODIMENTS

Figure 1:
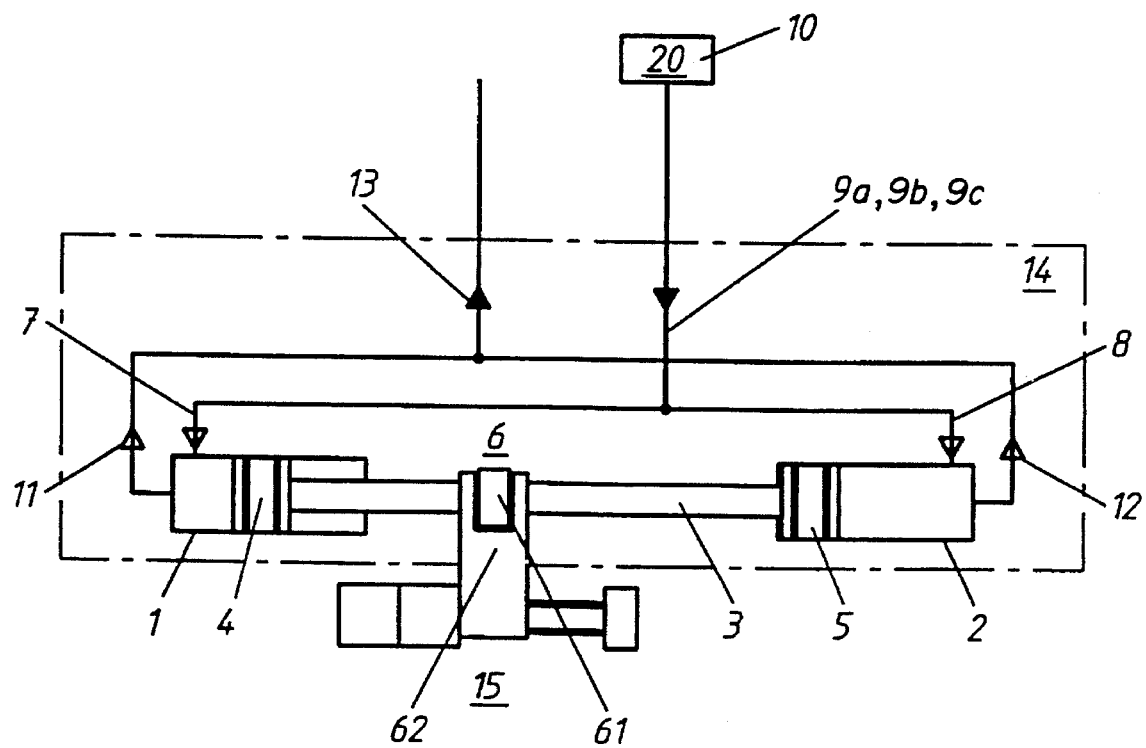
FIG. 1 is a simplified schematic drawing of a device in accordance with the invention.
Figure 2:
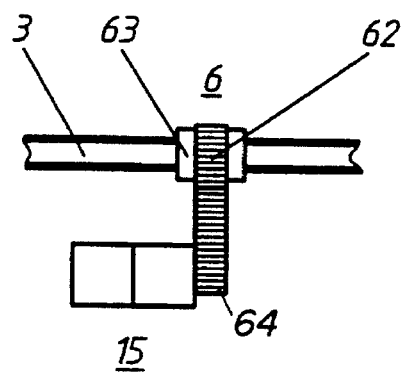
FIG. 2 is a modified detail of the device of FIG. 1.
Figure 3:
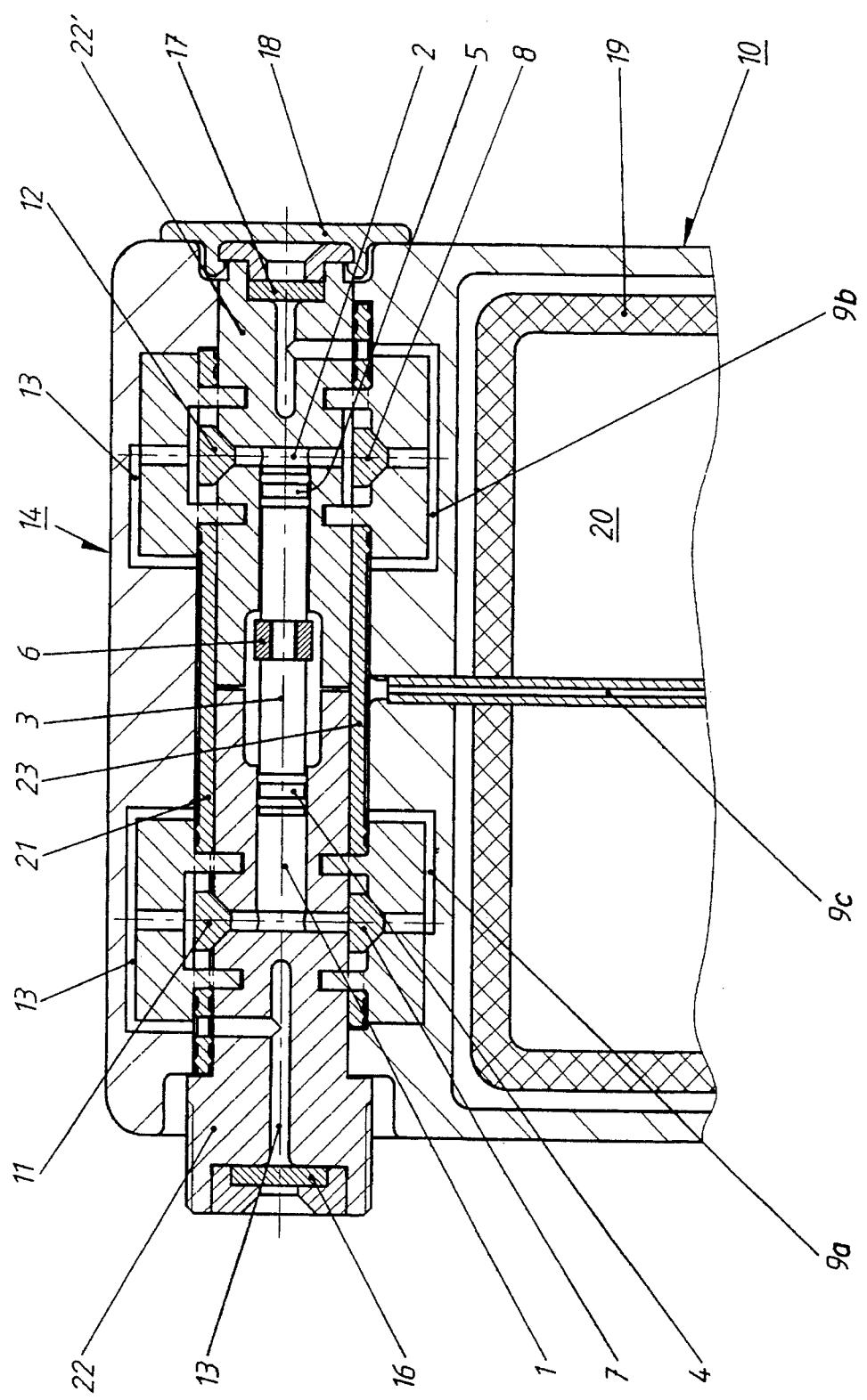
FIG. 3 is a sectional view of a device in accordance with the invention.

The device shown in FIGS. 1 through 3 serves to dispense a preselected dose of a liquid medicine and comprises a pump unit 14 connected to a medicine container 10.

Pump unit 14 comprises a double cylinder assembly having a left cylinder 1 and a right cylinder 2 formed in bodies 22 and 22', respectively, which cylinders receive the opposite ends of a double piston with displaceable left and right piston ends 4 and 5, respectively. The left and right piston ends 4 and 5 are rigidly joined together by a piston rod 3 and the piston ends are slideably mounted in the two cylinder parts 1, 2 so as to be reciprocatingly displaceable together in the same direction. Coupling means 6 is provided at the piston rod 3 and includes a drive disc 61 coupled to a drive fork 62 which links the piston rod to a drive unit 15 for mechanical driving. In the embodiment of FIG. 1, drive 15 includes a drive motor with an output shaft moving fork axially with respect to piston rod 3, thereby also moving the piston rod axially. However, the pistons in cylinders 1, 2 may also be displaced inductively by coupling a coil to the piston rod or an associated component, not shown.

Liquid flow in the pump is controlled in a wholly passive manner by means of two automatically closing intake valves 7 and 8 and two discharge valves 11 and 12. For that purpose a left intake valve 7 is provided for the left cylinder part 1 and a right intake valve 8 for the right cylinder part 2, the two intake valves 7, 8 being connectable by intake lines 9a, 9b and 9c to a medicine container 10 containing medicine 20. A left discharge valve 11 is provided for the left cylinder 1 and a right discharge valve 12 for the right cylinder 2, the two discharge valves 11, 12 supplying the liquid medicine 20 through a discharge line 13. Discharge line 13 is isolated from the external atmosphere by a pierceable membrane 16 through which may pass a catheter or cannula. Intake line 9b is similarly isolated from the external atmosphere by a pierceable membrane 17 which is covered by a snap-on cap 18 to prevent the patient removing liquid medicine 20 from medicine container 10.

Medicine container 10 contains a pouch 19 the interior of which is practically at vacuum when supplied. It is enough to pierce the membrane 17 using a syringe to fill pouch 19 through intake line 9 with liquid medicine 20. Thereafter, the pierced membrane 17 is securely closed by snap-on cap 18.

The automatic-control intake valves 7, 8 and the parts of the intake lines 9a, 9b and 9c which are around them are sealed by a semi-cylindrical rubber mat 23 from the two bodies 22 and 22' in which cylinders 1, 2 are formed. Mat 23 is formed with peripheral sealing ribs to permit communication between lines 9a, 9b and 9c but to prevent flow of liquid elsewhere. Similarly, automatic-control discharge valves 11, 12 and the parts of discharge line 13 around them are sealed by a rubber mat 21, shaped like mat 23, from bodies 22 and 22' of the cylinder 1, 2. In practice, valves 7 and 8 and mat 23 are made as a single body of resilient, elastomeric material having the central portion performing the sealing function of mat 23 and the end portions performing the valving functions. Mat 21 and valves 11 and 12 are similarly joined. The two rubber mats 21 and 23 therefore act as seals and valves.

A complete cycle of operation of pump unit 14 will now be described with reference to FIG. 3.

FIG. 3 shows the initial state wherein the two intake valves 7 and 8, and also the two discharge valves 11 and 12, are normally closed due to slight over-dimensioning of the resilient valve material. In a first step, double piston 4, 5 is moved to the left. This displacement of the double piston 4, 5 is by induction or else, as described above with reference to FIG. 1, is mechanical and is driven by means 6 coupled to piston rod 3. Discharge valve 12 remains closed but intake valve 8 is opened by a partial vacuum generated in right cylinder part 2, as a result of which liquid medicine 20 is sucked out of pouch 19 through intake lines 9c and 9b into right cylinder part 2.

Simultaneously, intake valve 7 remains closed by the combined forces of the pressure generated in left cylinder part 1 and the suction in intake line 9a, while the discharge valve 11 is opened by that pressure so that any air in the left cylinder part 1 is expelled through the discharge line 13 (by means of a catheter piercing the membrane 16).

In a second operating step after the double piston 4, 5 has reached its left end position, the piston is moved to the right again. This movement causes discharge valve 11 to be closed and intake valve 7 to open so that the liquid medicine 20 is sucked out of pouch 19 through intake line 9c into left cylinder chamber 1, while simultaneously intake valve 8 is closed and discharge valve 12 opened. The liquid medicine 20 which was sucked during the first phase into right cylinder chamber 2 is expelled through discharge line 13 past closed discharge valve 11 (by a catheter piercing membrane 16).

After the double piston 4, 5 has reached its right end position, it is again displaced to the left and the sequence of the first step is repeated, with the single difference that liquid medicine 20 is expelled from left cylinder chamber 1 rather than air.

In this manner the ganged right-left motion of the double piston 4, 5 implements repeated expulsion of liquid medicine 20 through the automatic valves 7, 8; 11, 12. The device thus delivers small doses at regular intervals which can be preset to occur, for example, between 30 seconds and 10 minutes. Taking into consideration the relatively slow uptake of medication into the human body, choosing the shortest intervals results in delivery of medication which is substantially continuous.

FIG. 2 shows an alternative delivery drive in which piston rod 3 is externally threaded or carries an externally threaded non-rotatable spindle 63 surrounded by an internally threaded, externally toothed gear 62. Gear 62 engages teeth on a gear 64 coupled to the output shaft of drive motor 15. When the output shaft of the motor rotates, gear 62 also rotates and the engaged threads cause spindle 63 to move axially somewhat in the manner of a nut, thus driving piston rod 3 and the pistons to dispense medication as described above.

What is claimed is:

1. A device for administering doses of liquid medicine of predetermined quantity comprising the combination of right and left cylinders (1, 2);

a substantially constant speed and force linear drive unit (15);

a double-ended piston (4, 5) having left and right piston ends displaceably mounted in said left and right cylinders, respectively;

means (6) for coupling said double-ended piston to said drive unit (15); and a pair each of automatically opening and closing intake valves (7, 8) and discharge valves (11, 12) for passively controlling the operation of said device.

2. A device according to claim 1 wherein said valves include a left intake valve (7) for said left cylinder and a right intake valve (8) for said right cylinder, said intake valves being connectable by an intake line (9a, 9b, 9c) to a medicine container (10), a left discharge valve (11) for said left cylinder and a right discharge valve (12) for the right cylinder, said discharge valves supplying liquid medicine through a discharge line (13).

3. A device according to claim 2 and including a piston rod (3) rigidly interconnecting said left piston end and said right piston end, said piston ends being displaceable in the same direction in said two cylinders.

4. A device according to claim 3 wherein said means for coupling said double ended piston to said drive unit (15) is mounted on said piston rod (3).

5. A device according to claim 4 wherein said means mounted on said piston rod for coupling said piston to said drive unit (15) includes a drive disk (61).

6. A device according to claim 4 wherein said means mounted on said piston rod for coupling said piston to a drive unit (15) includes a non-rotatable threaded spindle (63), an internally threaded gear (62) engaging said spindle and rotated by said drive unit (15).

7. A device according to claim 3 wherein said intake valves (7, 8) and said discharge valves (11, 12) are elastomeric bodies sealed passively.

8. A device according to claim 1 wherein said drive unit comprises a spindle and a nut threaded on said spindle.

9. A device for administering doses of liquid medicine of predetermined quantity comprising the combination of right and left cylinders (1, 2);

a drive unit (15);

a double-ended piston (4, 5) having left and right piston ends displaceably mounted in said left and right cylinders, respectively;

means (6) for coupling said double-ended piston to said drive unit (15);

a pair each of automatically opening and closing intake valves (7, 8) and discharge valves (11, 12) for passively controlling the operation of said device; and means for joining said cylinders, said double-ended piston, and said valves into a pump unit (14) detachably coupled to said drive unit (15).

10. A device according to claim 9 wherein said pump unit consists of injection-molded parts.

11. A device according to claim 9 and including a medicine container containing said liquid medicine for dispensing, and a snap-on cap (18) on said container for irreversibly securing against a patient's removal of liquid medicine (20) from said medicine container (10).

12. A device according to claim 9 wherein said double-ended piston includes a piston rod between said piston ends, and wherein said means for coupling said double-ended piston to said drive unit (15) is mounted on said piston rod (3).

13. A device according to claim 9 and including a piston rod (3) rigidly interconnecting said left piston end and said right piston end, said piston ends being displaceable in the same direction in said cylinders.

* * * * *